United States Patent [19]

Heinonen

[11] Patent Number: 5,337,738
[45] Date of Patent: Aug. 16, 1994

[54] FLUID VAPORIZING APPARATUS

[75] Inventor: Erkki Heinonen, Helsinki, Finland

[73] Assignee: Instrumentarium Corporation, Finland

[21] Appl. No.: 809,053

[22] Filed: Dec. 17, 1991

[30] Foreign Application Priority Data

Dec. 18, 1990 [FI]  Finland ................. 906254

[51] Int. Cl.[5] ............................................. A61M 17/00
[52] U.S. Cl. ........................... 128/203.12; 128/204.14;
128/203.14; 128/203.25; 261/DIG. 65
[58] Field of Search ........................ 128/203.12, 203.16,
128/203.17, 203.18, 203.25, 203.26, 204.13,
204.14, 204.21, 205.11, 205.24; 137/38; 261/96,
99, 102, 104, 105, DIG. 2, DIG. 65

[56] References Cited

U.S. PATENT DOCUMENTS

| | | | |
|---|---|---|---|
| 2,915,061 | 12/1959 | Edmondson et al. | 128/203.25 |
| 3,534,732 | 10/1970 | Bickford . | |
| 4,444,182 | 4/1984 | Gregory | 128/204.14 |
| 4,693,853 | 9/1987 | Falb et al. . | |
| 4,753,758 | 6/1988 | Miller . | |
| 4,879,997 | 11/1989 | Bickford | 128/203.12 X |
| 4,953,546 | 9/1990 | Blackmer et al. . | |
| 5,008,048 | 4/1991 | Ryder | 261/78.2 |

FOREIGN PATENT DOCUMENTS

| | | |
|---|---|---|
| 049067 | 7/1982 | European Pat. Off. . |
| 1917775 | 9/1970 | Fed. Rep. of Germany . |
| 0636854 | 5/1950 | United Kingdom ........... 128/203.12 |
| 968054 | 8/1964 | United Kingdom . |
| 1129194 | 3/1966 | United Kingdom . |
| 1148516 | 4/1969 | United Kingdom . |
| 1230972 | 5/1971 | United Kingdom . |
| 1312558 | 4/1973 | United Kingdom . |
| 1487042 | 9/1977 | United Kingdom . |
| 1491807 | 11/1977 | United Kingdom . |

*Primary Examiner*—V. Millin
*Assistant Examiner*—William M. Pierce
*Attorney, Agent, or Firm*—Andrus, Sceales, Starke & Sawall

[57] ABSTRACT

The invention relates to a fluid vaporizing apparatus (18), comprising a bottom section (28) and a cover section (27) enclosing a fluid chamber (33) containing fluid to be vaporized, and a gas chamber (34) into which fluid is vaporized, and a port (39) for discharging from gas chamber (34) the vapour evaporated from the fluid chamber. Said port (39) is located above the fluid level when the angle of inclination of the fluid vaporizing apparatus differs from the operating position of the apparatus by more than 45°. The invention relates also the use of a fluid vaporizing apparatus in the evaporation of anaesthetic fluids.

27 Claims, 9 Drawing Sheets

FLUID VAPORIZING APPARATUS

The present invention relates to a fluid vaporizing apparatus, comprising a bottom section and a cover section which enclose a fluid chamber containing a fluid to be vaporized, a gas chamber into which fluid vaporizes, and a port whereby the vapor vaporized from the fluid chamber is discharged through this port from the gas chamber. The invention relates also to the application of a fluid vaporizing apparatus in the vaporization of anaesthetic fluids.

The inhalation fluid vaporizers or fluid vaporizing equipment typically used in anaesthesia are intended for a particular inhalation fluid and coupled to a fresh gas circulation in a manner that all of the fresh gas flows through the vaporizer.

The internal structure of the apparatus is used to divide a fresh gas current into a primary and a secondary flow. The secondary flow passes through a fluid container included in the vaporizer, wherein it is saturated by inhalation vapor to a mixture of appr. 20%–35%, to an outflow included in the vaporizer. The primary flow passes directly to the outflow and, thus, does not contain any inhalation vapor. The high vapor content of the secondary flow is diluted by the primary flow, whereby the fresh gas flowing out of the vaporizer has a vapor content below 5%. A desired vapor content is obtained by adjusting the ratio between primary and secondary flows.

An apparatus as described above includes several weaknesses. Due to being intended for a particular inhalation fluid, several vaporizers, typically 3 vaporizers, are required. Each of these includes a flow control and regulation system, which are typically identical in terms of structure and only different from each other in terms of calibration. The result will be a bulky, heavy and expensive apparatus. As a result of the great weight, the replacement of a vaporizer is inconvenient and, therefore, there are often two or three of those installed ready for use. Being bulky and heavy, such devices require a lot of space and, thus, the entire fresh gas supply system will be bulky. Also required is a mechanism for preventing the simultaneous coupling of more than one vaporizer to the fresh gas circulation. Due to the great weight, also the filling of a vaporizer is often carried out with the vaporizer in its normal installed position. Thus, possible fluid splashes contaminate the respiratory air.

The bulkiness of a fresh gas supply system adds to the size of an entire anaesthesia machine, which further includes a ventilator and often also patient monitoring equipment. In addition, the disposition of a fresh gas supply system ergonomically in a central position leads to the disposition of other actuators all over the apparatus.

A passage of the entire fresh gas flow through a vaporizer results in a hazardous situation if a vaporizer is moved or held in a position other than upright: If any of the inhalation fluid finds its way into the primary flow circulation manifold, the fresh gas flowing out of the vaporizer can have an anaesthetic content of up to 35%, which as an instantaneous dose can be fatal for a patient. In addition, the oil used as an inhalation-fluid preservative may permanently block the primary flow manifold directing the entire fresh gas circulation to pass through a fluid container, which also leads to the above-described consequences. A similar hazardous situation results also if the entire anaesthesia machine is turned, e.g. for transportation, out of its basic position onto its side without the prior removal of fluid-containing vaporizers. Attempts have been made to resolve the above problems by replacing the traditional passive vapour-pressure based vaporization of inhalation fluid with the active injection based vaporization. Thus, the fluid is pumped by means of an electric pump or piston from a fluid container and injected through a nozzle in the form of droplets into a flow of fresh gas. A drawback in this apparatus is the demand of electrical energy, which increases susceptibility of the apparatus to malfunction. Pumping can also be effected by the application of compressed air. In this case, the precision of injection is affected e.g. by the amount of fluid in a container through the action of its hydrostatic pressure. This requires the compensation of pressure to comply with the fluid level, which leads to a complicated structure and, when using electronic compensation, also to dependence on the supply of electrical energy or alternatively a high pressure in the fluid container, which can also lead to serious consequences if a malfunction results in the uncontrolled discharge of pressure.

In another solution (U.S. Pat. No. 4,693,853), a fluid container and a flow control/regulation system are separated from each other in a manner that just the fluid container is removable while the rest of the mechanism is fixedly mounted on the apparatus. The fluid container intended for a particular inhalation fluid is provided with identification pins for mechanically changing the calibration of a flow regulation system to comply with a particular fluid. The apparatus only requires one flow control/regulation system. This reduces significantly the size, weight and price of a removable component. A removable fluid container is readily transportable and, thus, it can be easily re-filled elsewhere from the location of the apparatus itself so as to reduce the respiratory air contamination hazard caused by fluid splashes created during the course of filling.

A removable fluid container must be fluid-tight and gas-proof as it is detached from its location. In the cited solution, the fluid container is provided with closing ball valves for gas-flow inlet and outlet ports located in its cover, said valves closing automatically through the action of spring force as the fluid container is detached from its mounting. Due to the low viscosity and corrosiveness of inhalation fluids, the tightness or imperviousness of a fluid container, as it is for example upside down with connectors immersed in fluid, requires the use of expensive special materials.

An object of this invention is to eliminate the above problems. An object is to provide a fluid vaporizing apparatus which maintains fluid tightness when tilting the apparatus. A particular object is to provide a fluid vaporizing apparatus which is fluid-tight regardless of a holding position of the apparatus. A further object is to provide a fluid vaporizing apparatus which maintains fluid tightness without special materials in various holding positions.

The characterizing features of the invention are set forth in the annexed claims.

The basic idea of the invention is that a port for the gas discharging from a fluid vaporizing apparatus including a fluid chamber and a gas chamber is located above the fluid level, preferably in the centre of the apparatus or in the immediate vicinity thereof whereby, when the apparatus is tilted to an angle other than a normal position, the fluid contained therein does not flow into the port of the discharging gas.

Also, a port for the gas arriving in the apparatus is preferably located above the fluid level.

Thus, the port must lie above the fluid level whenever the apparatus is inclined 45° or more relative to its normal operating position. Preferably, the port is still lying above the fluid level whenever the apparatus is inclined 90°, i.e. it is lying on its side. In a particularly preferred case, the port is still lying above the fluid level whenever the apparatus is upside down. Thus, this invention also takes advantage of the partition of a fluid vaporizing apparatus into a fluid chamber and a gas chamber. The volume of a gas chamber exceeds that of a fluid space. The gas chamber has a volume which preferably is approximately 60% of the total volume of the apparatus, the fluid chamber having a remaining volume which is approximately 40% of the volume of the apparatus. Hence, in its most preferred embodiment, such an apparatus fit for vaporizing a fluid can be stored or carried in any desired position, i.e. even upside down or lying on its side.

In case the fluid vaporizing apparatus is removable, the gas ports can be further provided with shut-off elements, which make the apparatus gas-tight as it is detached.

The fluid vaporizing apparatus serves in anaesthesia as vaporizer or an evaporator, wherein the inhalation fluid is contained in a fluid chamber located in the bottom section of a container and vaporizes therefrom preferably by means of a fluid-vaporization activating element into a gas chamber located in the top section of the apparatus, whereby a gas preferably flowing therethrough is thus saturated with the inhalation vapour. Thereafter, the flow discharges from the fluid vaporizing apparatus to be diluted with a primary flow passing by the fluid container prior to its arrival in a ventilation unit.

In some cases, there is no need at all to pass a gas flow to a fluid vaporizing apparatus but a fluid contained inside the apparatus is allowed to boil for an increased pressure in the gas chamber. Through the action of pressure, the developed gas seeks a way out of the fluid vaporizing apparatus to mix subsequently with the actual gas flow delivered to a patient.

The invention will now be described in more detail with reference made to the accompanying drawings, in which.

Figure 1:
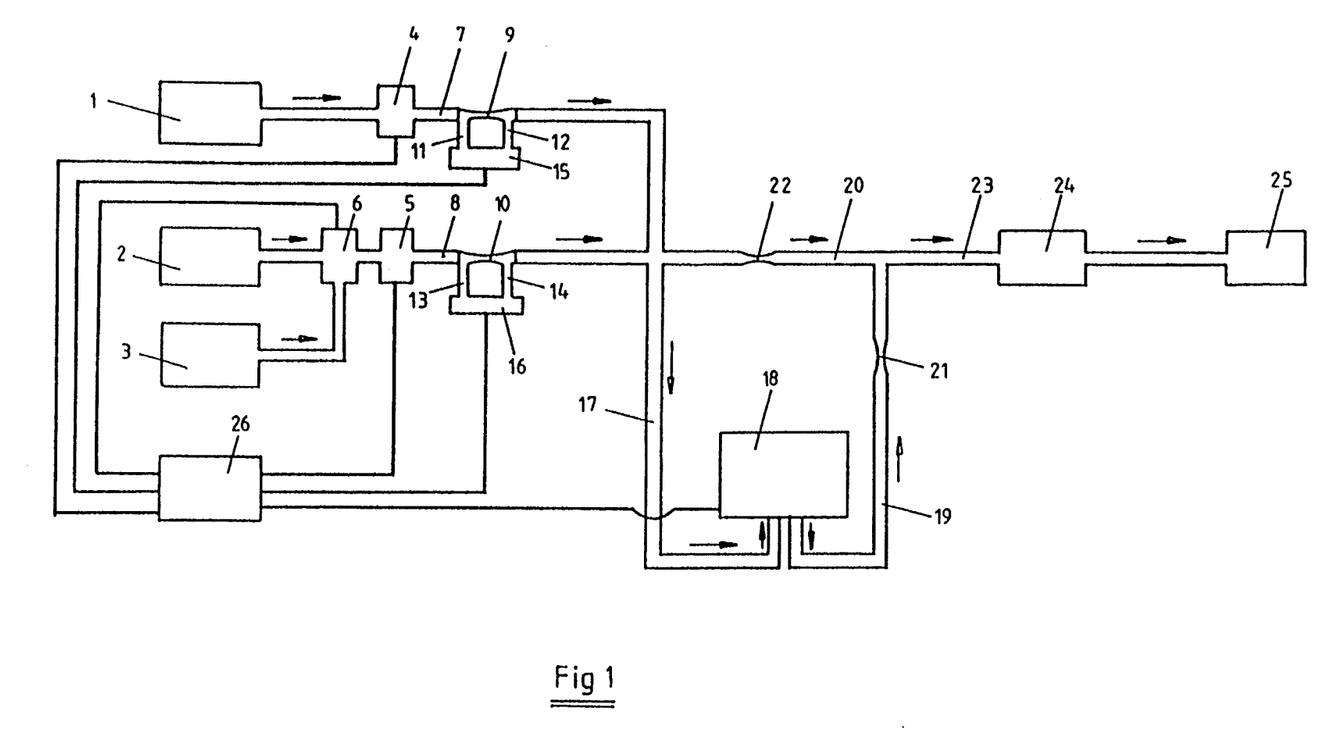
FIG. 1 is a schematic view showing an apparatus of the invention.

FIG. 1 primarily shows a schematic view of one preferred apparatus that can be used in the anaesthesia of a patient. In the apparatus, the elements regulating gas flows from containers 1, 2 and 3 comprise valves 4 and 5, preferably needle valves. The fresh gas comprises for example a mixture of either oxygen and an oxide of nitrogen or alternatively that of oxygen and air. Oxygen is contained in container 1, while container 2 contains the oxide of nitrogen and container 3 air. A valve 6 is operated to select either one of the gases of containers 2 or 3.

A tube 7 leading from container 1 and a tube 8 leading from containers 2 and 3 are fitted with flow restricting elements 9 and 10. From either side of these elements extend measuring ducts 11, 12, 13 and 14 to measuring elements 15 and 16, which are preferably pressure-difference measuring elements.

The tubes 7 and 8 extending from the containers join each other later and this combined flow of gases is divided into two components, i.e. a secondary flow and a primary flow. The secondary flow circulates along a tube 17 to a fluid vaporizing apparatus 18 of the invention and further along a tube 19 to join the primary flow running along a tube 20. Tube 19 is further fitted with a flow restricting element 21, whereby the secondary flow running through fluid vaporizing apparatus 18 can be controlled together with a flow restricting element 22 included in tube 20. The combined primary and secondary flow runs along a tube 23 to a ventilation unit 24 and further to a patient 25. The above described apparatus is controlled by a control element 26, preferably a microprocessor. From the control element there is preferably a connection to measuring elements 15 and 16. The control element also receives information about the fluid temperature contained in fluid vaporizing apparatus 18.

Figure 2:
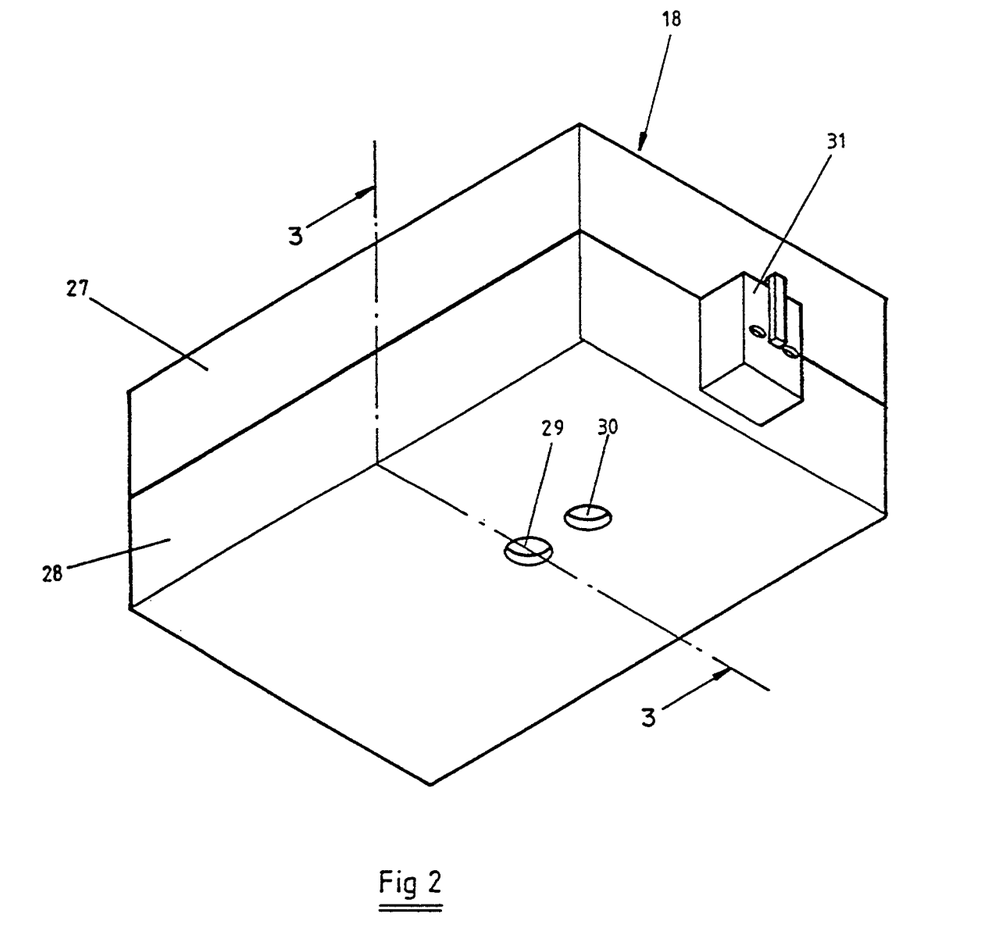
FIG. 2 shows a perspective view of one preferred fluid vaporizing apparatus of the invention, which is included in FIG. 1 and in this preferred case is removable.

FIG. 2 shows an external view of a highly preferred embodiment of a removable fluid vaporizing apparatus 18, provided with a cover section 27 and a bottom section 28. Preferably, the bottom of the apparatus is provided with two ports or openings 29 and 30, one for leading in the gas arriving along tube 17 and the other for leading out the gas circulated through the apparatus and further along tube 19 towards a patient. Outside the apparatus is shown one possible fluid supply element 31, useful for delivering more fluid.

Figure 3:
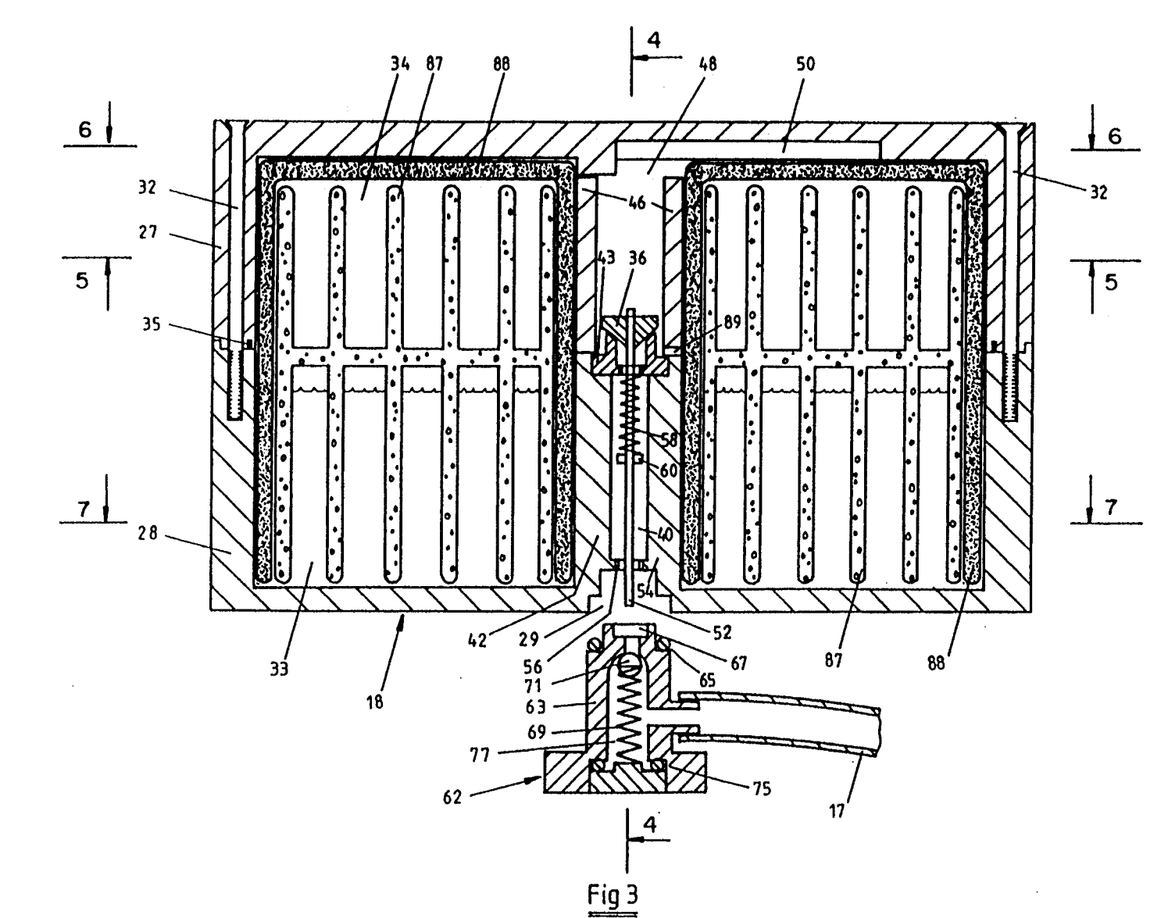
FIG. 3 shows the apparatus of FIG. 2 along a section 3—3.
Figure 4:
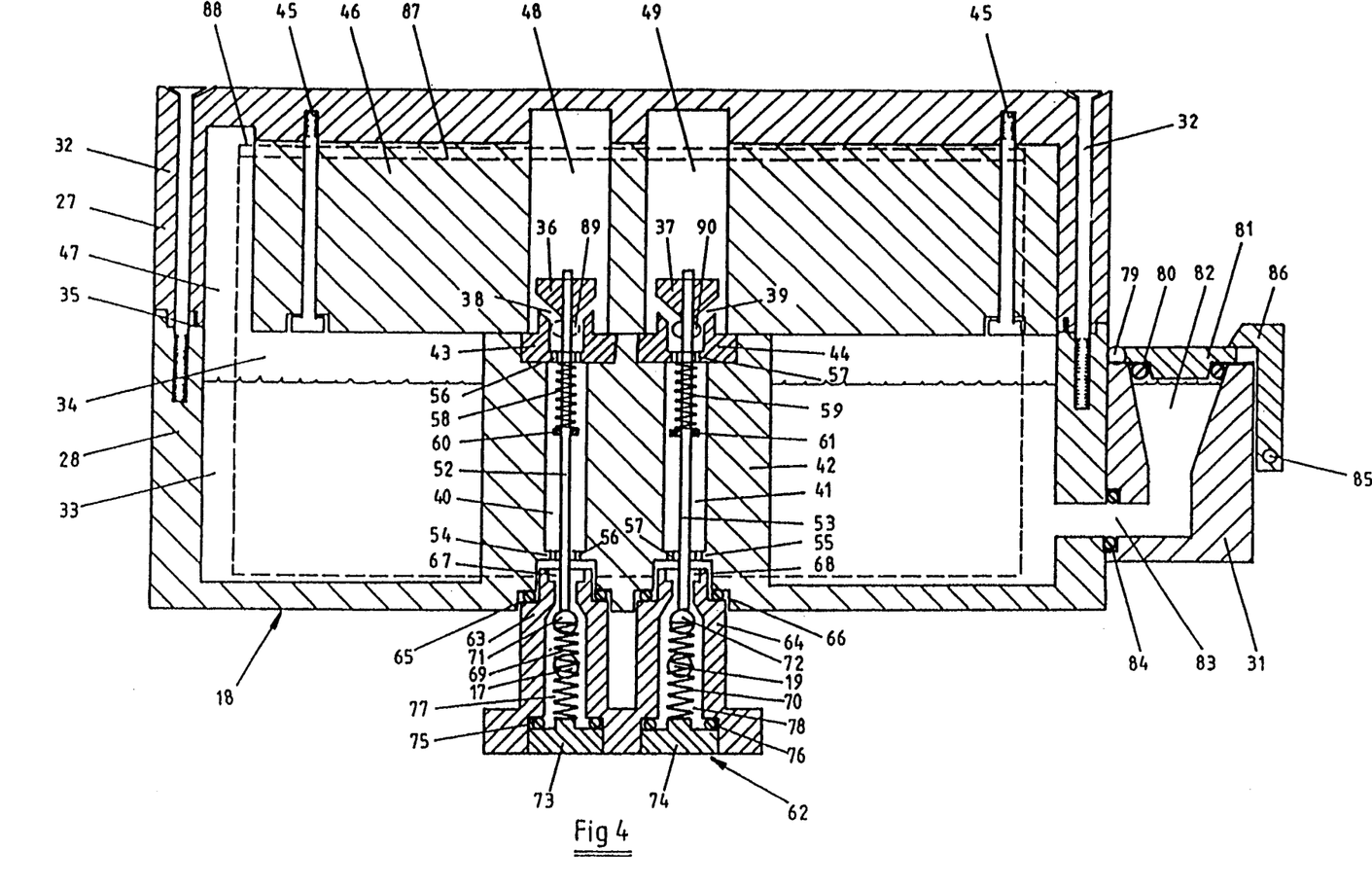
FIG. 4 shows the apparatus of FIG. 3 along a section 4—4 with the exception, however, that a separate connector is coupled to a fluid vaporizing apparatus.

FIGS. 3 and 4, which represent sectional views of a fluid vaporizing apparatus 18, illustrate preferred structural designs for the apparatus. A cover section 27 and a bottom section 28 are fastened to each other with screws 32 and enclose a fluid chamber 33 and a gas chamber 34. The junction between cover section and bottom section is further provided with a seal or a packing 35 to make sure of a fluid-tight apparatus.

Figure 8:
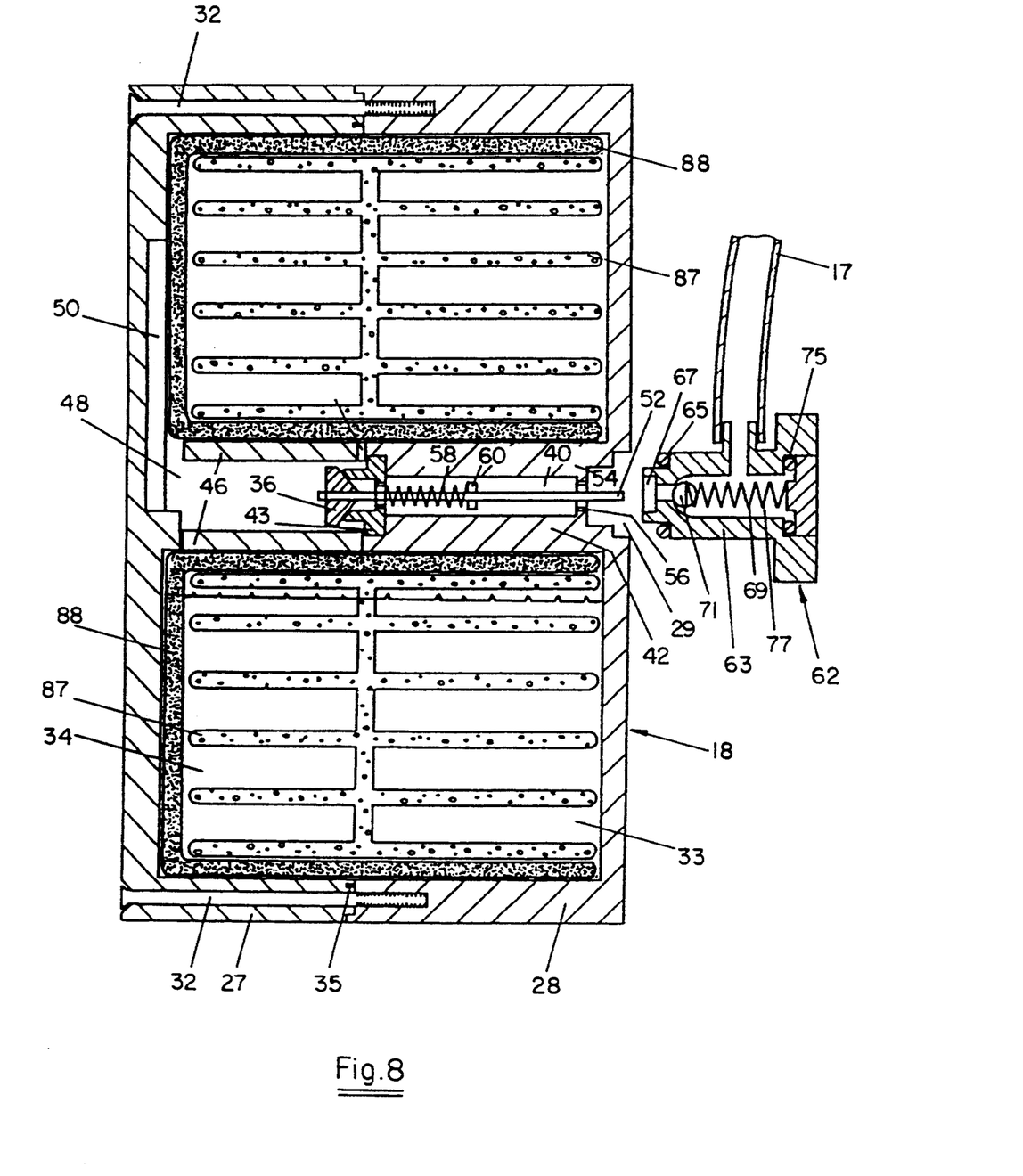
FIG. 8 shows the apparatus in a different orientation than in FIGS. 3 and 4.

Disposed in the centre of apparatus 18 are shut-off elements 36 and 37 for closing and opening a gas inlet and outlet. Since the fluid vaporizing apparatus 18 has a fluid volume less than a half of the entire container volume, said shut-off elements 36 and 37 can be arranged according to the invention in a manner that those elements, or ports 38 and 39 produced upon the opening thereof, are always located above the fluid level regardless of the position of apparatus 18. Thus, it is not possible to set a fluid vaporizing apparatus in a position that would bring the ports into a direct contact with fluid. See FIG. 8. Hence, the fluid vaporizing apparatus 18 can be stored in any desired position, say during transportation.

In view of having shut-off elements 36 and 37 always above the fluid level regardless of the position of the apparatus, there should be a flow communication from these shut-off elements to gas inlet port 29 and outlet port 30, preferably through the intermediary of tubular ducts 40 and 41. The ducts are included in an elevation 42 which is preferably integral with bottom section 28, whereby the number of junctions brought into contact with fluid remains as few as possible. At the top edge of the elevation, the end portions of ducts 40 and 41 are fitted with special shut-off element counter-members 43 and 44, which are seated therein and against which said shut-off elements 36 and 37 are pressed to prevent the flow of incoming and discharging gas through ports 38 and 39.

Figure 5:
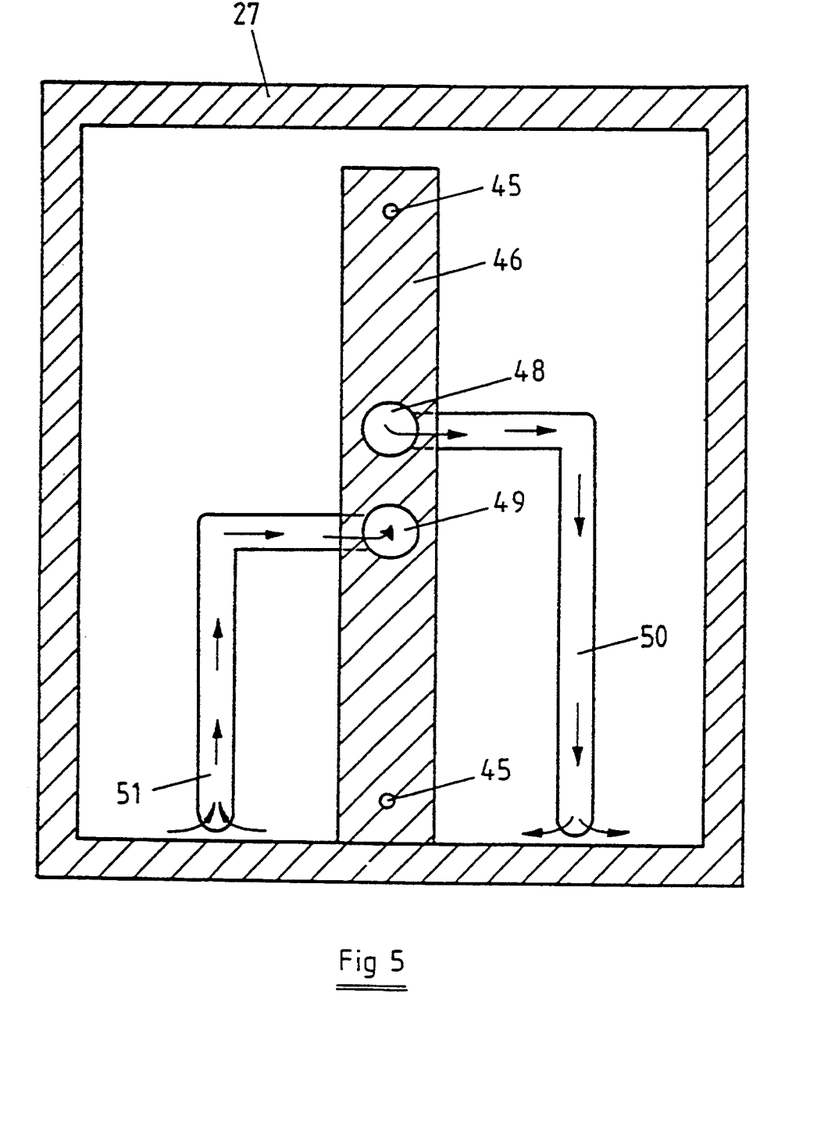
FIG. 5 shows the apparatus of FIG. 3 along a section 5—5 after a vaporization activating element included inside the apparatus as well as a gas-flow controlling element are removed.
Figure 6:
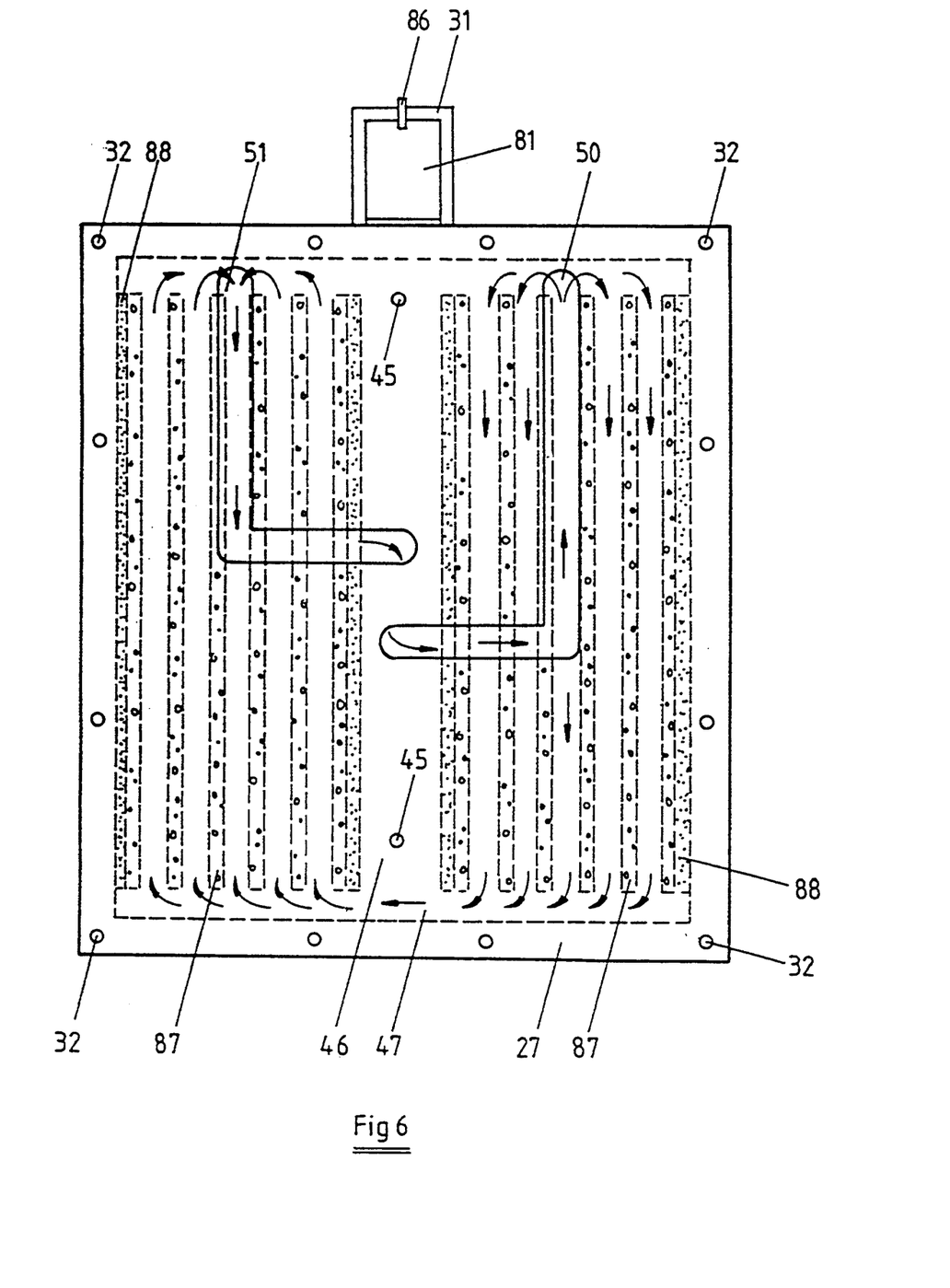
FIG. 6 shows the apparatus of FIG. 3 along a section 6—6.

To the cover section 27 of fluid vaporizing apparatus 18 is fastened with screws 45 a partition 46, which preferably extends in the direction of a desired flow from one edge of the cover section to the vicinity of the opposite edge, leaving there nevertheless a gap or opening 47 for the gas flowing from one side of the partition to the other, as shown in FIGS. 4 and 6. This partition is partially pressed against the opposite elevation 42 and shut-off element counter-members 43 and 44 seated on top of the elevation. Thus, the counter-members need not necessarily be otherwise attached to the elevation. Inside said partition 46 extend flow ducts 48 and 49, which are in communication with gas chamber 34 preferably by way of slots 50 and 51 made in the surface of cover section 27 mounted on the top section of the gas chamber, said slots being more clearly shown in FIGS. 5 and 6.

Particularly, FIGS. 3 and 6 illustrate the division of gas chamber 34 into two sections by means of partition 46. This is preferred whenever said shut-off elements 36 and 37 are located in the centre of fluid vaporizing apparatus 18, as seen in both lateral and vertical direction. Since said slots 50 and 51, made in the surface of the cover section, one slot directing the flowing gas in and the other out, open on different sides of the partition, the flowing gas can be forced to travel first through one section of the gas chamber and thereafter through a gap 47 formed by the partition and the end edge of the cover section into a gas chamber lying on the other side of the partition and, after passing through the latter, the gas flow finds its way out through slot 51.

In order to control said shut-off elements 36 and 37 such elements are provided with axles 52 and 53, which preferably extend to the ports 29 and 30 of the tubular ducts. In order to maintain the axles laterally in a proper direction, said axles are adapted to pass through guides 54 and 55 extending across the ducts. These guides are provided with flow conduits 56 and 57 in order not to block the flow proceeding in the tubular ducts.

The axles are provided with springs 58 and 59, which allow a movement occurring in the direction of tubular ducts 40 and 41 and which are preferably wound around the axles between the guides and stoppers 60 and 6i included in the guides. The purpose of these springs is to limit the movement of said shut-off elements and also to close said ports 38 and 39 located between shut-off elements 36 and 37 and shut-off element counter-members 43 and 44, as a connector 62 is uncoupled off said ports 29 and 30.

A connector 62 shown in FIGS. 3 and 4 comprises tip portions 63 and 64 fitting in ports or openings 29 and 30 in the bottom of an apparatus suitable for the vaporization of a fluid. In order to eliminate possible leaks in the junctions between the tip portions and the ports fitting against them, the tip portions are surrounded by seals or packings 65 and 66. On the other hand, the tip portions include openings 67 and 68, behind which are balls 71 and 72 pressed against the edges of the surrounding ports by the action of springs 69 and 70. The other end of the springs is secured to base members 73 and 74, which are also surrounded by packings 75 and 76 to prevent gas leaks to the environment from spaces 77 and 78 located between the balls and the base members. The gas flows into space 77 through tube 17 and out of space 78 through tube 19.

When coupling said connector 62 to ports 29 and 30 included in fluid vaporizing apparatus 18, the tips of axles 52 and 53 extending in tubular ducts 40 and 41 are pressed against balls 71 and 72, whereby the axles strive to move away from the balls within the range allowed by springs 58 and 59. Hence, this creates ports 38 and 39 between the shut-off elements carried at the ends of the axles and the counter-members therefor, said ports providing a flow communication to a gas chamber located inside the apparatus. When springs 58 and 59 are sufficiently compressed, the movement of axles comes to an end and the balls 71 and 72 blocking said connector openings 67 and 68 strive in turn to move backwards as springs 69 and 70 are yielding, thus establishing a connection from spaces 77 and 78 also to a fluid vaporizing element.

Thus, a single coupling action is sufficient to achieve a gas flow from tube 17 into a fluid vaporizing element and from there into tube 19 and further to patient 25. When connector 62 is uncoupled from fluid vaporizing apparatus 18, said shut-off elements 36 and 37 are pressed against counter-members 43 and 44 and block all flows into and out of said apparatus 18. Also, a flow occurring through the connector during the course of uncoupling is blocked as well, since springs 69 and 70 serve to press balls 71 and 72 against the edges of openings 67 and 68.

The fluid vaporizing apparatus 18 is supplied with fluid preferably from a fluid supply means 31. On top of it is a gate 81, which is openable on a hinge 79 and surrounded by a sealing 80 and through which the supply of fluid proceeds into a vessel 82, the latter being in flow communication by way of a passage 83 with a fluid chamber 33 included in apparatus 18. The passage is surrounded by a sealing 84 at the junction of fluid vaporizing apparatus 18 and fluid supply means 31. The gate can be locked by means of lever 86 operable on a hinge 85.

Figure 7:
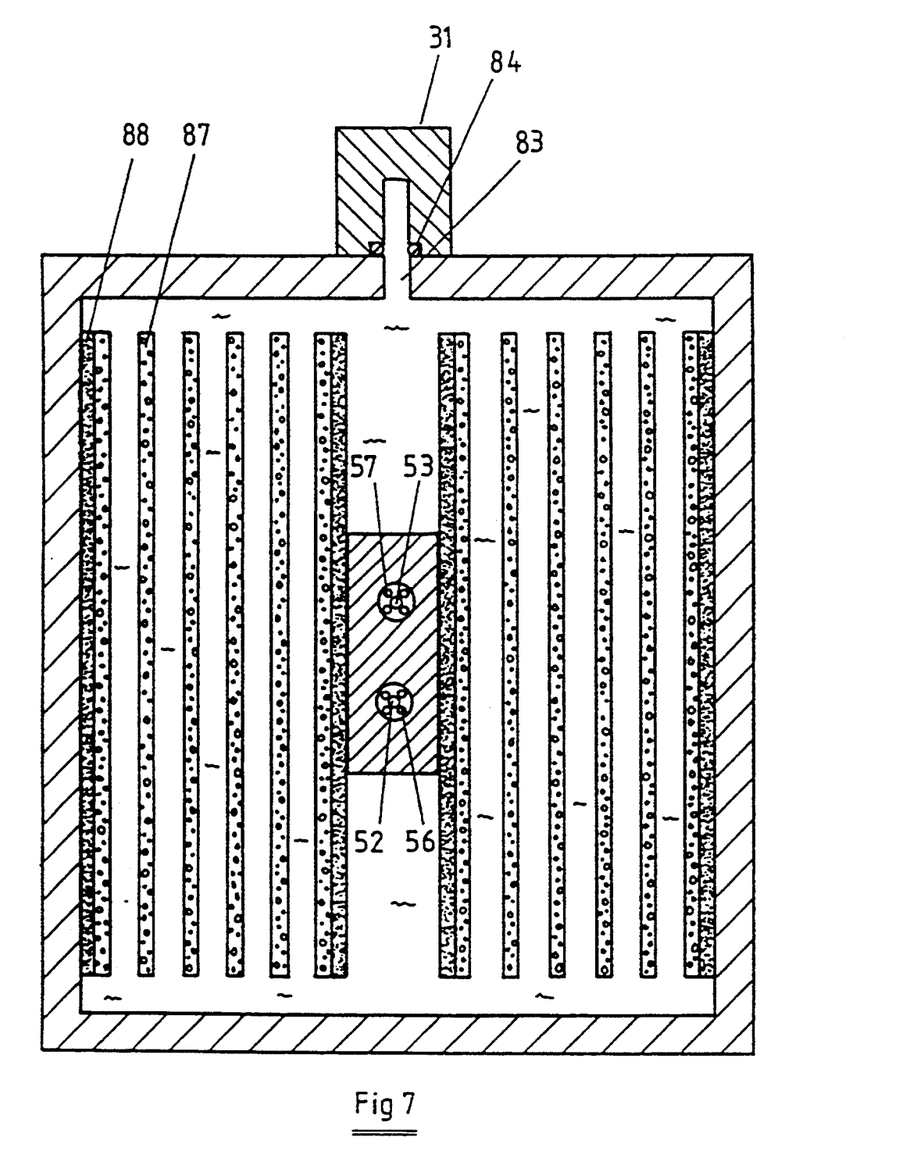
FIG. 7 shows the apparatus of FIG. 3 along a section 7—7.

FIGS. 3 and 7, in particular, illustrate a fluid-vaporization activating element 87 and a gas-flow controlling element 88 included in fluid vaporizing apparatus 18 according to a preferred embodiment. For the sake of clarity, FIGS. 4 and 6 include dash-and-dot lines showing the disposition of such elements inside apparatus 18, although said elements are not shown in the actual sectional figures.

The fluid-vaporization activating element 87 extends from fluid chamber 33 to gas chamber 34, carrying fluid up over to the side of the gas chamber where it is vaporized from the surface of element 87 to mix with surrounding gas. In order to achieve an effective vaporization, said vaporization activating element must have a large surface and, in a preferred case, the surface of said element is provided with a lot of corrugations, a gas flow conforming itself therewith. As for its structure, said element is preferably made of a porous and cellular material. The most essential duty of a gas-flow controlling element 88 is to guide a flow arriving in and discharging from apparatus 18 to run in slots 50 and 51 made in the cover section for achieving a desired flow pattern also in actual gas chamber 34, as shown in FIGS. 5 and 6. Thus, the gas flow arriving along flow duct 48 passes along slot 50 in cover section 27 to a starting point, which is preferably the edge of the cover section and from which, by the action of this upcoming edge, it descends lower into gas chamber 34 and continues therefrom, as shown by the arrows in the figures, its passage below gas-flow controlling element 88 being in conformity with the surfaces of vaporization activating element 87, to the opposite end of the gas chamber. There, the direction of the gas flow deflects through an opening 47 formed by the edge of the cover section and partition 46 over to the other side of said partition where the gas flow continues its passage, this time in opposite direction, still in conformity with the surfaces of fluid-vaporization activating element 87 to the opposite end of the cover section. At this point, the flow can only continue its passage upwards into a slot 51 remaining between gas-flow controlling element 88 and cover section 27, said slot extending to a flow duct 49 passing through partition 46 and further along tube 19 to a patient.

The gas-flow controlling element is preferably made of a material capable of carrying fluid from one place to another. Such a material often contains fibrous pores, one example of such a material being felt. Thus, a porous material extending all the way to the fluid chamber strives at the same time to carry fluid from fluid chamber 33 into gas chamber 34. Thus, on its part, the duty of such material is to increase in the gas chamber the concentration of fluid vaporizing from the fluid chamber.

Figure 9:
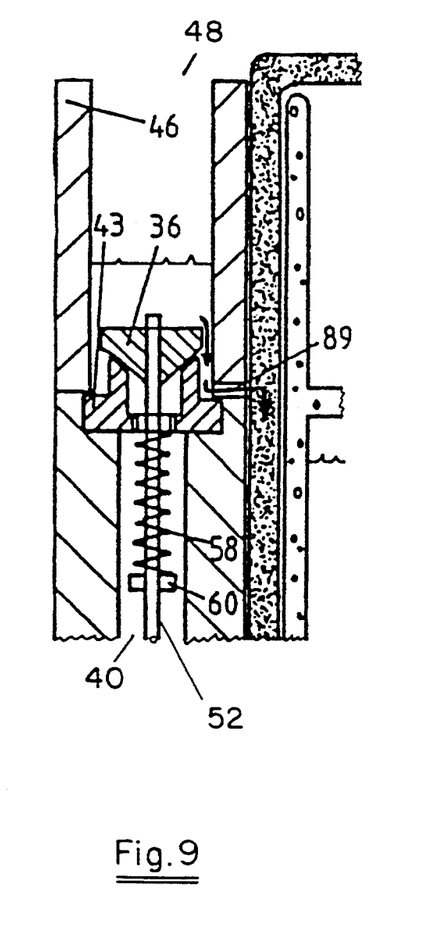
FIG. 9 is a fragmentary view showing the operation of drains in the apparatus.

An advantage gained by a porous material used as gas-flow controlling element 88 over a fluid non-absorbable material is also that a porous material absorbs away e.g. the fluid retained in slots 50 and 51 and flow ducts 48 and 49 during transportation of the apparatus in upside down position and prevents it from entering e.g. in tube 19 leading to a patient. In order to make it possible to remove also the fluid trapped in flow ducts 48 and 49 while the apparatus is in an operating position, these ducts must be provided with fluid drain openings 89 and 90, as shown in FIGS. 3, 4 and 9. Preferably, these openings should be located below a gap formed between the shut-off element and the cover section during the coupling of connector 62. Furthermore, the drain openings preferably extend to that side of partition 46, in which said slots 50 and 51 serving as extensions of flow ducts are located. For this reason, in FIG. 4, the circumference of drain opening 89, which is not actually visible in this section, is indicated with dots. As can be concluded on the basis of FIG. 3, said drain opening in FIG. 4 faces towards the viewer, i.e. unlike said drain opening 90.

Another significant advantage gained by a porous material for gas-flow controlling element 88 is that such material absorbs the fluid through drain openings 89 and 90 away from flow ducts 48 and 49 but, at the same time, prevents the flow of gas through these drain openings. Thus, it is preferable that a porous material be tightly packed against the drain openings. In the solution shown in the figures, the tightness is simply achieved by placing a fixed fluid-vaporization activating element 87 in a space between the edge connected by cover section and bottom section and partition 46 and thereafter by lining the fluid-vaporization activating element with a porous material having a thickness which is preferably equal to or greater than the width of a space remaining unused in this situation.

The invention is by no means limited to the above embodiments but various details of the invention can be modified within the scope of the claims. The most essential feature in view of the invention is that a port 39 for discharging the fluid from a fluid-vaporizing apparatus is located above the fluid level when tilting said apparatus 18 or regardless of its position. A second port 38 for receiving the inflowing gas in the apparatus is not necessarily required. This is particularly the case when the fluid contained in the fluid chamber is allowed to boil, whereby the developing gas pressure is sufficient to exhaust the vapour out of apparatus 18 along tube 20 to mix with the flowing gas. Thus, a tube 17 leading to the fluid vaporizing element is not required but the gas going to a patient flows entirely along tube 20.

Although, in the solution described in reference with the figures, a connector 62 is coupled to ports 29 and 30 in the bottom of a fluid vaporizing apparatus 18, such ports could well be located in any desired side face of the apparatus. The essential feature is that shut-off elements 36 and 37 or ports 38 and 39 to be closed thereby are located above the fluid level with the apparatus in an inclined position. In the most preferred case, the ports are located sufficiently close to the centre of a fluid vaporizing apparatus whereby, regardless of the position of apparatus 18, the shut-off elements or ports do not end up below the fluid level.

The shut-off elements 36 and 37 as well as connector 62 shown in the figures are highly preferred in terms of construction but some other solutions are also available. Neither are the axles leading to shut-off elements necessary for the structure of apparatus 18. In one alternative solution, the coupling of connector 62 could be effected directly to a shut-off element and, thus, tubular ducts 40 and 41 would not actually be required. In that case, one of the walls of a fluid vaporizing apparatus should have a shape curving towards the centre of the apparatus.

I claim:

1. Fluid vaporizing apparatus (18) for developing vapor and supplying same to a conduit for delivery to a patient in course of his/her respiration, said apparatus comprising:

a container formed of a bottom part (28) and a top part (27), said container being positionable, in use, in a normal operating orientation in which said bottom part is beneath said top part, said container having an internal chamber of predetermined size, said internal chamber having a central portion located centrally in said internal chamber, said internal chamber being divided into a first chamber portion (33) and a second chamber portion (34), said first chamber portion forming a liquid chamber portion when said apparatus is in the normal operating orientation and being fillable with a liquid to be vaporized to a predetermined level below the central portion of said internal chamber, said second chamber portion forming a gas chamber portion above said first chamber portion when said apparatus is in the normal operating orientation to receive vapor, the liquid in said first chamber portion presenting a liquid surface within said chamber which is exposed to said second chamber portion when said apparatus is in the normal operating orientation;

at least one port means (39) by which the apparatus may be coupled to the conduit, said port means having valve means with an opening discharging vapor from said second chamber portion to the conduit and a shut off element blocking and unblocking said opening, said valve means being positioned in the central portion of said internal chamber, the predetermined size of said internal chamber being such that said valve means is above the exposed liquid surface in said internal chamber when said apparatus is inclined from the normal operating orientation; and gas flow directing means for dividing said second chamber portion into first and second, adjacent, interconnected sections and for forming a plurality of generally parallel vapor flow paths that are horizontally spaced from each other when said apparatus is in the normal operating orientation.

2. A fluid vaporizing apparatus as set forth in claim 1 wherein said gas flow directing means includes a partition means (46) for forming said first and second sections in said second chamber portion.

3. A fluid vaporizing apparatus as set forth in claim 2 wherein said gas flow directing means includes gas flow controlling means (88) in each of said sections extending along the direction of gas flow in said sections, said gas flow controlling means having a generally U-shape cross-section transverse to the flow direction for lining walls of said sections.

4. A fluid vaporizing apparatus as set forth in claim 1 wherein said gas flow directing means is formed to flow gas in one direction in one of said sections and flow as in the opposite direction in the other of said sections.

5. A fluid vaporizing apparatus as set forth in claim 1 wherein said gas flow directing means includes gas flow controlling means (88) in each of said sections extending along the direction of gas flow in said sections, said gas flow controlling means having a generally U-shaped cross-section transverse to the flow direction for lining walls of said sections.

6. A fluid vaporizing apparatus as set forth in claim 1 wherein said apparatus has a further port means (38), said further port means supplying gas to said second chamber portion to receive vapor, said further port means having valve means with an opening supplying the gas to said second chamber portion and a shut off element blocking and unblocking said opening, said valve means of said further port means being positioned in the central portion of said chamber at a location at which said valve means is above the exposed liquid surface in said chamber when said apparatus is inclined from said normal operating orientation.

7. A fluid vaporizing apparatus as set forth in claim 6 wherein said one port means is in fluid communication with one of said sections and said other port means is in fluid communication with the other of said sections.

8. A fluid vaporizing apparatus as set forth in claim 6 further defined as apparatus for developing an anaesthetic vapor from a liquid to be vaporized.

9. A fluid vaporizing apparatus as set forth in claim 6 wherein said further port means has a passage means (42) forming a passage from said opening in said valve means of said further port means to the exterior of the apparatus.

10. A fluid vaporizing apparatus as set forth in claim 9 wherein said passage means of said further port means includes connector means for connection to mating connector means of the conduit.

11. A fluid vaporizing apparatus as set forth in claim 10 wherein said further port means has a rod means extending through said passage means for engagement with said mating connector means for operating said shut off element of said valve means of said further port means.

12. A fluid vaporizing apparatus as set forth in claim 6 further including further flow duct means (48) forming a passage from said opening in said valve means of said further port means to said second chamber portion.

13. A fluid vaporizing apparatus as set forth in claim 12 wherein said further flow duct means surrounds said opening in said valve means of said further port means and contains a drain (89) below said opening of said valve means of said further port means for draining liquid found in said further flow duct means into said first chamber portion when the apparatus is in the normal operating orientation.

14. A fluid vaporizing apparatus as set forth in claim 13 wherein said drain (89) of said further flow duct means has associated therewith means (88) for absorbing liquid passing through said drain while blocking the passage of gas through said drain.

15. A fluid vaporizing apparatus as set forth in claim 12 wherein said second chamber portion has a slot (50) in a wall element thereof extending from said further flow duct means into said second chamber portion for supplying gas to said second chamber portion.

16. A fluid vaporizing apparatus as set forth in claim 15 wherein said slot has an end terminating in said second chamber portion and an end terminating at said further flow duct means and wherein said apparatus includes gas flow controlling means (88) for directing gas supplied by said further port means from said end of said slot terminating at said further flow duct to said end of said slot terminating in said second chamber portion.

17. A fluid vaporizing apparatus as set forth in claim 16 wherein said gas flow controlling means (88) is formed of material capable of absorbing liquid and carrying same from one place to another within said apparatus.

18. A fluid vaporizing apparatus as set forth in claim 1 wherein said port means has a passage means (41) forming a passage from said opening in said valve means to the exterior of the apparatus.

19. A fluid vaporizing apparatus as set forth in claim 18 wherein said passage means includes connector means for connection to mating connector means of the conduit.

20. A fluid vaporizing apparatus as set forth in claim 19 wherein said port means has a rod means extending through said passage means for engagement with said mating connector means for operating said shut off element of said valve means.

21. A fluid vaporizing apparatus as set forth in claim 1 further including flow duct means (49) forming a passage from said opening in said valve means to said second chamber portion.

22. A fluid vaporizing apparatus as set forth in claim 21 wherein said flow duct means surrounds said opening and contains a drain (90) below said opening for draining liquid found in said flow duct means into said first chamber portion when said apparatus is in the normal operating orientation.

23. A fluid vaporizing apparatus as set forth in claim 22 wherein said drain (90) has associated therewith means (88) for absorbing liquid passing through said drain while blocking the passage of gas through said drain.

24. A fluid vaporizing apparatus as set forth in claim 21 wherein second chamber portion has a slot (51) in a wall element thereof extending from said flow duct means into said second chamber portion for collecting vapor from said second chamber portion.

25. A fluid vaporizing apparatus as set forth in claim 24 wherein said slot has an end terminating in said second chamber portion and an end terminating at said flow duct means and wherein said apparatus includes gas flow controlling means (88) for directing vapor in said second chamber portion to said end of said slot terminating in said second chamber portion.

26. A fluid vaporizing apparatus as set forth in claim 25 wherein said gas flow controlling means (88) is formed of material capable of absorbing liquid and carrying same from one place to another within said apparatus.

27. A fluid vaporizing apparatus as set forth in claim 1 further defined as apparatus for developing an anaesthetic vapor from a liquid to be vaporized.

* * * * *

UNITED STATES PATENT AND TRADEMARK OFFICE
CERTIFICATE OF CORRECTION

PATENT NO. : 5,337,738
DATED     : August 16, 1994
INVENTOR(S) : Heinonen

It is certified that error appears in the above-indentified patent and that said Letters Patent is hereby corrected as shown below:

TITLE PAGE:
[56] REFERENCES CITED:

FOREIGN PATENT DOCUMENTS

| 814,426 | United Kingdom | 6/1959 |
| 758,657 | United Kingdom | 10/1956 |
| 682,519 | United Kingdom | 11/1952 |

IN THE CLAIMS

CLAIM 4, Col. 9, Line 38, delete "as" and substitute therefor ---gas---;

Signed and Sealed this

Ninth Day of May, 1995

Attest:

BRUCE LEHMAN

*Attesting Officer*   *Commissioner of Patents and Trademarks*